US006714841B1

(12) United States Patent
Wright et al.

(10) Patent No.: US 6,714,841 B1
(45) Date of Patent: Mar. 30, 2004

(54) HEAD CURSOR CONTROL INTERFACE FOR AN AUTOMATED ENDOSCOPE SYSTEM FOR OPTIMAL POSITIONING

(75) Inventors: James Wright, Santa Barbara, CA (US); Hamid Wasti, Sacramento, CA (US); Darrin R. Uecker, Santa Barbara, CA (US)

(73) Assignee: Computer Motion, Inc., Goleta, CA (US)

( * ) Notice: Subject to any disclaimer, the term of this patent is extended or adjusted under 35 U.S.C. 154(b) by 0 days.

(21) Appl. No.: 09/179,039

(22) Filed: Oct. 26, 1998

Related U.S. Application Data

(63) Continuation of application No. 08/904,047, filed on Jul. 31, 1997, now Pat. No. 5,911,036, which is a continuation of application No. 08/529,095, filed on Sep. 15, 1995, now Pat. No. 5,825,982.

(51) Int. Cl.[7] .................. G05B 15/00; G05B 19/04; A61B 5/05; A61B 1/00
(52) U.S. Cl. .................. 700/259; 700/264; 700/258; 700/251; 600/407; 600/118
(58) Field of Search .................. 700/259, 264, 700/258, 251; 600/407, 118

(56) References Cited

U.S. PATENT DOCUMENTS

| 977,825 | A | 12/1910 | Murphy |
|---|---|---|---|
| 3,171,549 | A | 3/1965 | Orloff |
| 3,280,991 | A | 10/1966 | Melton et al. |
| 4,058,001 | A | 11/1977 | Waxman |
| 4,128,880 | A | 12/1978 | Cray, Jr. |
| 4,221,997 | A | 9/1980 | Flemming |
| 4,367,998 | A | 1/1983 | Causer |
| 4,401,852 | A | 8/1983 | Noso et al. |
| 4,456,961 | A | 6/1984 | Price et al. |
| 4,460,302 | A | 7/1984 | Moreau et al. |
| 4,474,174 | A | 10/1984 | Petruzzi |
| 4,491,135 | A | 1/1985 | Klein |
| 4,503,854 | A | 3/1985 | Jako |
| 4,517,963 | A | 5/1985 | Michel |

(List continued on next page.)

FOREIGN PATENT DOCUMENTS

| DE | U 9204118.3 | 7/1992 |
|---|---|---|
| DE | 4310842 C2 | 1/1995 |
| EP | 0239409 A1 | 9/1987 |

(List continued on next page.)

OTHER PUBLICATIONS

"Endocorporeal Surgery Using Remote Manipulators" (Ned S. Rasor and J.W. Spickler) Remotely Manned Systems—Exploration and Operation in Space, California Institute of Technology 1973.

(List continued on next page.)

*Primary Examiner*—George B. Davis
(74) *Attorney, Agent, or Firm*—Townsend and Townsend and Crew LLP

(57) ABSTRACT

A medical system that is coupled to an endoscope which provides a video image to a monitor. The system includes an electrical circuit to overlay a graphic image onto the video image provided by the endoscope. The endoscope is moved by a robotic arm.

25 Claims, 4 Drawing Sheets

U.S. PATENT DOCUMENTS

| | | |
|---|---|---|
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Andersson et al. |
| 4,815,450 A | 3/1989 | Patel |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,442,728 A | 8/1995 | Kaufman et al. |
| 5,443,484 A | 8/1995 | Kirsch et al. |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,458,574 A | 10/1995 | Machold et al. |
| 5,476,010 A | 12/1995 | Fleming et al. |
| 5,490,117 A | 2/1996 | Oda et al. |
| 5,490,843 A | 2/1996 | Hildwein et al. |
| 5,506,912 A | 4/1996 | Nagasaki et al. |
| 5,512,919 A | 4/1996 | Araki |
| 5,515,478 A | 5/1996 | Wang |
| 5,524,180 A * | 6/1996 | Wang et al. ................. 600/118 |
| 5,544,654 A | 8/1996 | Murphy et al. |
| 5,553,198 A | 9/1996 | Wang et al. |
| 5,562,503 A | 10/1996 | Ellman et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,837 A | 12/1997 | Green |
| 5,718,038 A | 2/1998 | Takiar et al. |
| 5,735,290 A | 4/1998 | Sterman et al. |
| 5,749,362 A | 5/1998 | Funda et al. |
| 5,754,741 A | 5/1998 | Wang et al. |
| 5,776,126 A | 7/1998 | Wilk et al. |
| 5,779,623 A | 7/1998 | Bonnell |
| 5,800,423 A | 9/1998 | Jensen |

| | | | |
|---|---|---|---|
| 5,807,284 A | | 9/1998 | Foxlin |
| 5,807,378 A | | 9/1998 | Jensen et al. |
| 5,808,665 A | * | 9/1998 | Green .......................... 348/65 |
| 5,810,880 A | | 9/1998 | Jensen et al. |
| 5,813,813 A | | 9/1998 | Daum et al. |
| 5,814,038 A | | 9/1998 | Jensen et al. |
| 5,815,640 A | * | 9/1998 | Wang et al. ................. 700/251 |
| 5,817,084 A | | 10/1998 | Jensen |
| 5,825,982 A | * | 10/1998 | Wright et al. ............... 700/259 |
| 5,841,950 A | * | 11/1998 | Wang et al. ................. 700/264 |
| 5,859,934 A | | 1/1999 | Green |
| 5,876,325 A | | 3/1999 | Mizuno et al. |
| 5,878,193 A | * | 3/1999 | Wang et al. ................. 700/251 |
| 5,882,206 A | | 3/1999 | Gillio |
| 5,887,121 A | | 3/1999 | Funda et al. |
| 5,907,664 A | * | 5/1999 | Wang et al. ................. 700/251 |
| 5,920,395 A | * | 7/1999 | Schulz ....................... 365/622 |
| 5,931,832 A | | 8/1999 | Jensen |
| 5,950,629 A | | 9/1999 | Taylor et al. |
| 6,024,695 A | | 2/2000 | Taylor et al. |
| 6,201,984 B1 | * | 3/2001 | Funda et al. ................. 600/407 |
| 6,463,361 B1 | * | 10/2002 | Wang et al. ................. 700/258 |

FOREIGN PATENT DOCUMENTS

| | | |
|---|---|---|
| EP | 0424687 A1 | 5/1991 |
| EP | 0776738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

"A Survey Study of Teleoperators, Robotics, and Remote Systems Technology" (Arthur D. Alexander, III) Remotely Manned Systems—Exploration and Operation in Space, California Institute of Technology 1973.

"Impacts of Telemation on Modern Society" (Arthur D. Alexander, III), On the Theory and Practice of Robots and Manipulators vol. II, 1974.

Transcript of a video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine".

Statutory Declaration of Dr. Philip S. Green, presenter of the video entitled "Telepresence Surgery—The Future of Minimally Invasive Medicine".

Abstract of a presentation "Telepresence: Advanced Teleoperator Technology for Minimally Invasive Surgery" (P. Green et al.) given at the 3rd World Congress of Endoscopic Surgery in Bordeaux, Jun. 18–20, 1992.

Abstract of a presentation "Telepresence: Advanced Teleoperator Technology for Minimally Invasive Surgery", (P. Green et al.) given at "Medicine meets virtual reality" symposium in San Diego, Jun. 4–7, 1992.

Abstract of a presentation "Camera Control for Laparoscopic Surgery by Speech–Recognizing Robot: Constant Attention and Better Use of Personnel" (Colin Besant et al.) given at the 3rd World Congress of Endoscopic Surgery in Bordeaux, Jun. 18–20, 1992.

"A Literature Review: Robots in Medicine" (B. Preising et al.) IEEE Jun. 1991.

"Robots for the Operating Room" (Elizabeth Corcoran), The New York Times, Sunday Jul. 19, 1992, Section 3, p. 9, col. 1.

"Taming the Bull: Safety in a Precise Surgical Robot" (Russell H. Taylor et al.), IEEE 1991.

Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18–20, 1992.

Abstract of a presentation "3–D Vision Technology Applied to Advanced Minimally Invasive Surgery Systems" given at the 3rd World Congress of Endoscopic Surgery in Bordeaux, Jun. 18–20, 1992.

"Analysis of the Surgeon's Grasp for Telerobotic Surgical Manipulation" (Frank Tendick and Lawrence Stark), IEEE 1989.

"Kinematic Control and Visual Display of Redundant Teleoperators" (Hardi Das et al.), IEEE 1989.

"A New System for Computer Assisted Neurosurgery" (S. Lavallee), IEEE 1989.

"An Advanced Control Micromanipulator for Surgical Applications" (Ben Gayed et al.), Systems Science vol. 13 1987.

"Force Feedback–Based Telemicromanipulation for Robot Surgery on Soft Tissues" (A.M. Sabatini et al.), IEEE 1989.

"Six–Axis Bilateral Control of an Articulated Slave Manipulator Using a Cartesian Master Manipulator" (Masao Inoue), Advanced Robotics 1990.

"On a Micro–Manipulator for Medical Application—Stability Consideration of its Bilateral Controller" (S. Majima et al.), Mechatronics 1991.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon–Machine Interface for Teleoperated Microsurgery" (Steve Charles M.D. et al.), IEEE 1989.

"A Robot in an Operating Room: A Bull in a China Shop" (J.M. Dolan et al.), IEEE 1987.

Abstract of a presentation "Concept and Experimental Application of a Surgical Robotic System the Steerable MIS Instrument SMI" given at the 3rd World Congress of Endoscopic Surgery in Bordeaux, Jun. 18–20, 1992.

Abstract of a presentation given at the 3rd World Congress of Endoscopic Surgery in Bordeaux, Jun. 18–20, 1992, entitled "Session 15/1".

Abstract of a presentation "A Pneumatic Controlled Sewing Device for Endoscopic Application the MIS Sewing Instrument MSI" given at the 3rd World Congress of Endoscopic Surgery in Bordeaux, Jun. 18–20, 1992.

Abstract of a presentation given at the 3rd World Congress of Endoscopic Surgery in Bordeaux (Jun. 18 to 20, 1992), entitled "Session 15/2".

Abstract of a presentation given at the 3rd World Congress of Endoscopic Surgery in Bordeaux (Jun. 18 to 20, 1992), entitled Session 15/4.

Abstract of a presentation given at the 3rd World Congress of Endoscopic Surgery in Bordeaux (Jun. 18 to 20, 1992), entitled "Session 15/5".

"Properties of Master–Slave Robots" (C. Vibet), Motor–con 1987.

"A New Microsurgical Robot System for Corneal Transplantation" (Noriyuki Tejima), Precision Machinery 1988.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis" (H. Kazerooni), IEEE 1989.

"Power and Impedance Scaling in Bilateral Manipulation" (J. Edward Colgate), IEEE 1991.

"S.M.O.S.: Stereotaxical Microtelemanipulator for Ocular Surgery" (Aicha Guerrouad and Pierre Vidal), IEEE 1989.

"Motion Control for a Sheep Shearing Robot" (James P. Trevelyan et al.), Proceedings of the 1st International Symposium on Robotics Research, MIT, Cambridge, Massachusetts, USA, 1983.

"Robots and Telechirs" (M.W. Thring), Wiley 1983.

Industrial Robotics (Gordon M. Mair), Prentice Hall 1988 (pp. 41–43, 49–50, 54, 203–209 enclosed).

"Student Reference Manual for Electronic Instrumentation Laboratories" (Wolf et al.), Prentice Hall, New Jersey 1990, pp. 498 amd 499.

"Surgery in Cyberspace" (Taubes), Discover Magazine, Dec. 1994.

* cited by examiner

HEAD CURSOR CONTROL INTERFACE FOR AN AUTOMATED ENDOSCOPE SYSTEM FOR OPTIMAL POSITIONING

CROSS-REFERENCE TO RELATED APPLICATIONS

This application is a continuation application of application Ser. No. 08/904,047, filed Jul. 31, 1997, U.S. Pat. No. 5,911,036, which is a continuation application of application Ser. No. 08/529,095, filed Sep. 15, 1995, now U.S. Pat. No. 5,825,982.

BACKGROUND OF THE INVENTION

1. Field of the Invention

The present invention relates to a graphical user interface that can be remotely controlled by a surgeon to control various devices and conditions of an operating room.

2. Description of Related Art

To reduce the invasiveness of surgery, endoscopes are commonly utilized to view the internal organs of a patient. One end of the endoscope contains a lens which is inserted into the patient through a small incision of the skin. The lens focuses an image that is transmitted by fiber optic cable to a camera located at the opposite end of the endoscope. The camera is coupled to a monitor that displays a video image of the patient.

The endoscope can be used in conjunction with another surgical instrument that is inserted into the patient. An assistant typically holds the endoscope while the surgeon manipulates the surgical instrument. The assistant moves the endoscope in response to instructions from the surgeon. Any mis-communication between the surgeon and the assistant may result in an error in the movement of the endoscope, thereby requiring the surgeon to repeat the instruction. Additionally, holding the endoscope for a significant amount of time may cause the assistant to become fatigued.

U.S. application Ser. No. 07/927,801 discloses a robotic arm that holds and moves an endoscope in response to commands from the surgeon. The commands are provided through a hand controller or a foot pedal. The controller and pedal require coordinated movements which may detract the surgeon from the surgical procedure. It would be desirable to provide an interface that manipulates a robotically controlled surgical device while requiring minimal physical coordination by the surgeon. Additionally, it would be desirable to provide a single interface that allows the surgeon to control a number of devices such as an operating table, laparoscopic camera, laser tool, etc.

SUMMARY OF THE INVENTION

The present invention is an interface that allows a surgeon to remotely control surgical devices and conditions of an operation room. The surgeon views a video image that is displayed by a monitor. The monitor may be coupled to a video device such as a laparoscopic camera that is attached to the end of an endoscope. Static graphic images and a dynamic graphic cursor are overlayed onto the video image. The graphic cursor has a pixel location on the monitor which corresponds to a spatial location of a pointer signal. The pointer signal is transmitted by a transmitter worn on the head of the surgeon. The pointer signal may be a laser which is directed to a screen that is located adjacent to a detection camera. The surgeon may move the graphic cursor relative to the video image by tilting his head and varying the spatial location of the pointer signal. The interface may have a controller which generates output signals in response to the movement of the pointer signal. The output signals may move a robotic arm which controls the position of the endoscope. The controller may also generate command signals when the graphic cursor is moved into a static graphic image. The command may vary a condition of the operating room such as the position of the operating table.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
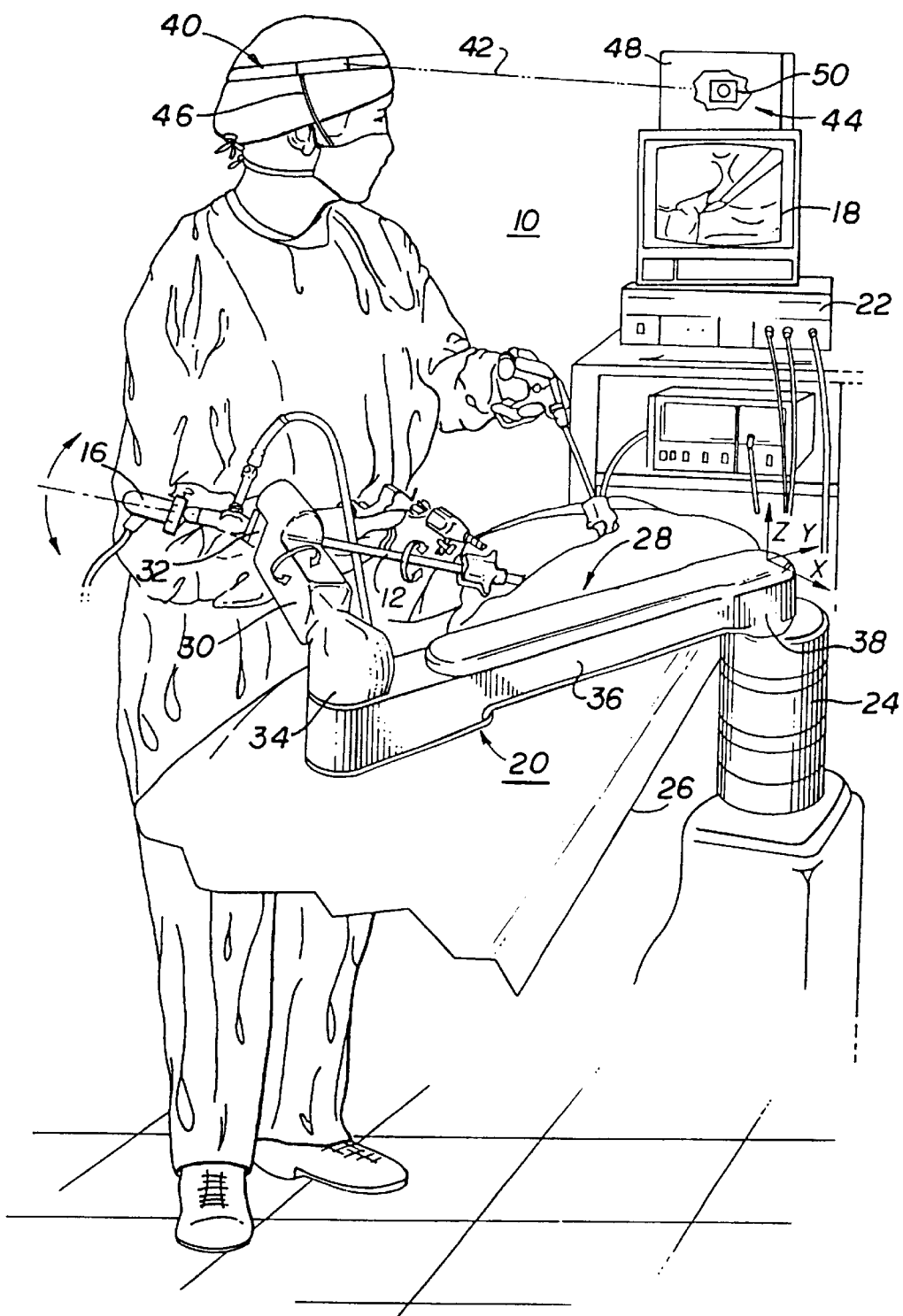
FIG. 1 is a perspective view of a robotic system that controls an endoscope.

Referring to the drawings more particularly by reference numbers, FIG. 1 is a robotic system 10 that controls a surgical instrument 12. The surgical instrument 12 is typically an endoscope that is inserted into a patient. The tip of the endoscope typically has a lens(es) that focuses an image of the patient. The endoscope 12 may also have fiber optic cable that transmits the image to a camera 16 located at the end of the scope. The camera 16 is typically a charge coupled device (CCD). The camera 16 is coupled to a monitor 18 which displays the image.

The instrument 12 is moved by a robotic arm assembly 20 that is coupled to a computer 22. In the preferred embodiment the robotic assembly 20 has a linear actuator 24 that is mounted to a surgical table 26. The linear actuator 24 moves a linkage arm assembly 28 in a linear manner relative to the table 26. The linear actuator 24 defines an origin of a fixed first coordinate system that has a first x axis, a first y axis and a first z axis.

The linkage arm assembly 28 contains a first linkage arm 30 attached to an end effector 32. The first linkage arm 30 is mounted to a first rotary actuator 34 which can rotate the arm. The first rotary actuator 34 is attached to a second linkage arm 36. The second linkage arm 36 is mounted to a second rotary actuator 38 that can rotate the arms. The rotary actuator 38 is attached to the output shaft of the linear actuator 24.

Figure 2:
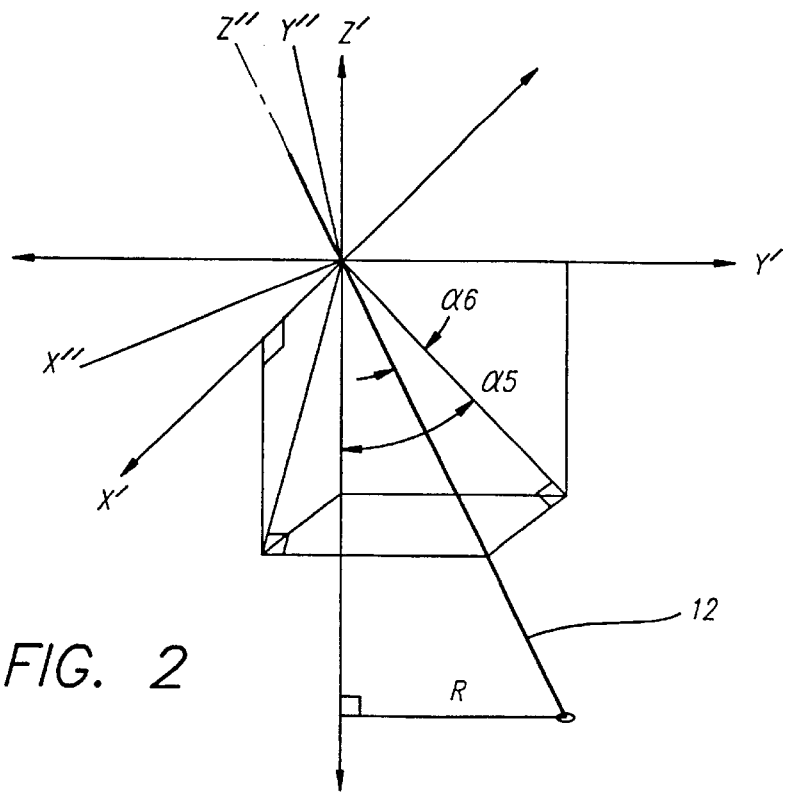
FIG. 2 is a schematic of an endoscope within two different coordinate systems.

The end effector 32 is typically coupled to a pair of passive joints (not shown) that allow rotation of the instrument as indicated by the arrows in FIG. 1. The end effector 32 may also have a worm gear (not shown) that rotates the endoscope about the longitudinal axis of the instrument. As shown in FIG. 2, the junction of the instrument 12 and the end effector 32 define the origin of a second coordinate system which has a second x axis (x'), a second y axis (y') and a second z axis (z'). The junction of the end effector 32 and the instrument 12 also define a third coordinate system which has a third x axis (x"), a third y axis (y") and a third z axis (z"). The zag axis is always parallel with the longitudinal axis of the instrument 12. The actuators receive input signals from the computer 22 to control the movement of the robotic arm assembly 20.

Referring to FIG. 1, the surgeon wears a transmitter unit 40 that transmits a pointer signal 42 which is received by a receiver unit 44. The transmitter unit 40 is preferably a laser pointer which emits a laser beam 42. The laser pointer may have a blow switch 46 that allows the surgeon to turn the laser on and off by blowing or drawing in the air of a tube located adjacent to the surgeons mouth. The transmitter 40 may be a laser switch sold by Point Source, Inc. of Germantown, Ohio. Although a laser transmitter is shown and described, the transmitter may be an acoustic or electromagnetic device that generates a wave that is detected by an appropriate detector(s). It being understood that any system that can detect a physical movement of the surgeon is encompassed by the present invention.

The receiver unit 42 preferably includes a screen 48 that is in the field of view of a camera 50. The laser beam 42 creates an illuminated dot on the screen 48 which is then detected by the camera 50. The camera 50 is preferably a charged coupled device (CCD). When the surgeon moves his head, the pointer signal 42 moves to a new spatial location on the screen 48. The surgeon can therefore control the position of the illuminated dot by tilting his head.

Figure 3:
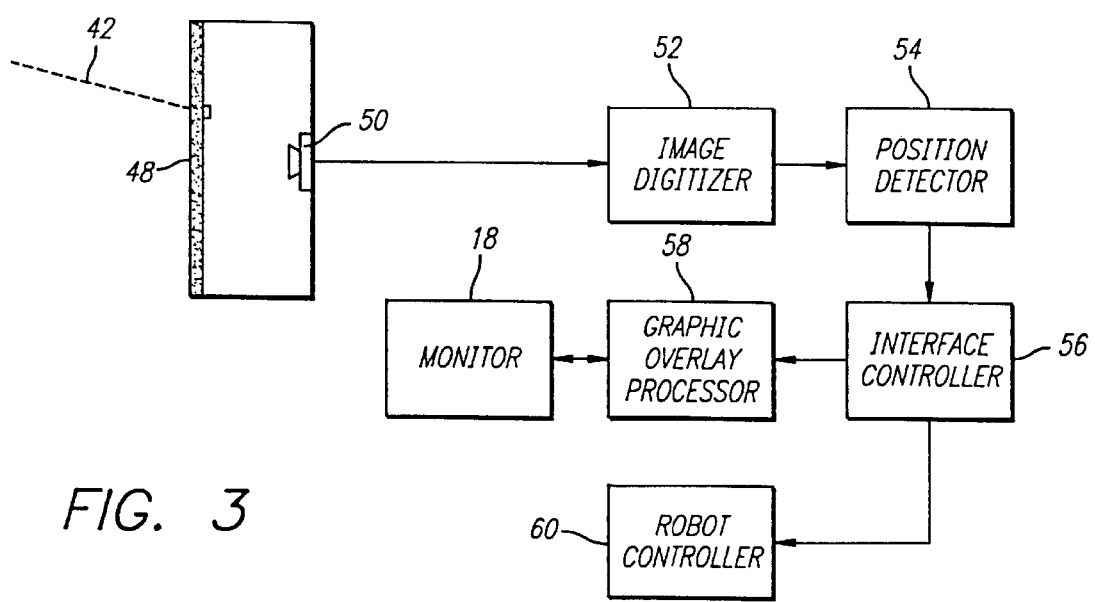
FIG. 3 is a schematic of a head cursor interface electrical circuit.

As shown in FIG. 3, the CCD camera 50 is coupled to an image digitizer 52 which digitizes the images provided by the camera 50. The digitizer 52 provides digitally based values that correspond to the light intensity detected by each pixel of the camera 50. The digitizer 52 is coupled to a position detector 54 which detects the spatial location of the pointer signal 42 relative to the screen 48. The detector 54 first compares the intensity values of each pixel with a threshold value. The detector 54 provides an associated value of 1 for each pixel that has an intensity which exceeds the threshold value, and a value of 0 for each pixel which is below the threshold value. The threshold value is selected to correspond to the intensity of an illuminated dot created by the laser beam 42 striking the screen 50. The threshold value is preferably large enough to filter out background light.

After each pixel is assigned a 1 or 0 value, the x and y spatial coordinates of the pointer signal 42 relative to the screen 48 is computed by determining the center of mass of the pixels which have an assigned value of 1 in accordance with the following equations.

$$Mx = \frac{\sum_{i-n,j-m} x_i \cdot O(i,j)}{\sum_{i-n,j-m} O(i,j)}$$

$$My = \frac{\sum_{i-n,j-m} y_j \cdot O(i,j)}{\sum_{i-n,j-m} O(i,j)}$$

where;

Mx=the x coordinate of the center of mass.

My=the y coordinate of the center of mass.

O(i,j)=the assigned value of the pixels i through j.

Xi=the x coordinate of the pixels i through n.

Yj=the y coordinate of the pixels j through m.

The x and y spatial coordinates generated by the detector 54 are provided to an interface controller 56. The interface controller 56 maps the x and y spatial coordinates generated by the detector to corresponding pixel locations on the monitor 18. The interface controller 56 is coupled to a graphic overlay processor 58 and a robot controller 60. The graphic overlay processor 58 is coupled to the monitor 18. Although separate controllers are shown and described, it is to be understood that the blocks depicted are merely functional and that the operations may be performed by a single microprocessor or different combinations of processors.

Figure 4:
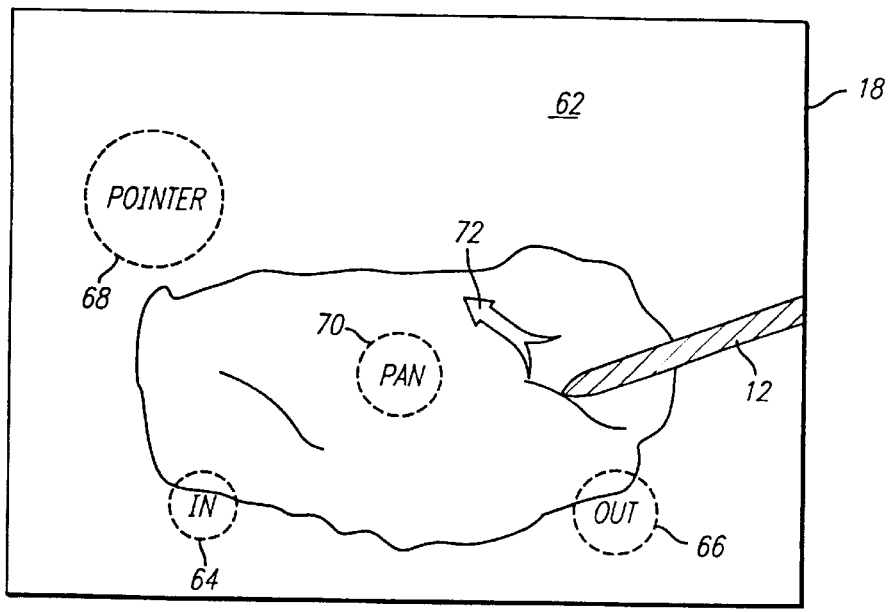
FIG. 4 is a front view of a monitor which displays a video image and a plurality of graphical overlays.

As shown in FIG. 4, the monitor 18 displays a video image 62 provided by the camera 16 of the endoscope 12. The video image 62 is typically an internal organ of a patient. The graphic overlay processor 58 generates a series of static graphic images 64–70 that overlay onto the video image 62 displayed by the monitor 18. The overlay processor 58 also generates a dynamic graphic cursor 72 that can move across the monitor 18. The graphic cursor 72 may move in conjunction with any movement of the laser beam 42 emitted from the pointer 40 mounted to the surgeon's head.

To move the cursor 72, the surgeon may move his head and vary the spatial location of the pointer signal 42 on the screen 48. The new pointer location is detected by the CCD camera 50. The position detector 54 computes the x and y spatial coordinates which are then provided to the interface controller 56. The interface controller 56 maps the new x and y spatial coordinates to pixel locations on the video image 62. The controller 56 then provides the new pixel locations to the graphic overlay processor 58 which displays the cursor 72.

The interface controller 56 may also generate output signals to move the robotic arm assembly 20 in conjunction with the position of the cursor 72. For example, the interface controller 56 may generate output signals to move the robotic arm 20 and endoscope 12 and to move the video image in the direction of the cursor. In this manner, the surgeon can view a new location within the patient by merely moving his head. Although a cursor 72 is shown and described, it is to be understood that the surgeon may move the robotic arm 20 and the video image 62 without a cursor 72 by merely tilting his head and watching the displayed image on the monitor 18.

The static graphic images 64–70 may provide input commands to control various devices such as the robotic arm assembly 20. For example, the graphic images 64 and 66 provide ZOOM IN and ZOOM OUT commands for the video image. When the surgeon moves the cursor 72 into the area of the IN graphic image 64, the interface controller 56 generates output signals to move the robotic arm 20 so that the end of the endoscope moves closer to the object displayed by the monitor 18. Likewise, when the cursor 72 is moved into the OUT graphic 66, the controller 56 generates output signals to move the robotic arm 20 so that the endoscope moves away from the object shown on the monitor 18.

To determine the interaction between the cursor 72 and the graphic images 64–70, the interface controller 56 compares the pixel locations that correspond to the x and y coordinates provided by the detector 54 with a group of pixel locations associated with each graphic image. If the x and y pixel locations associated with the pointer signal equal a pixel location of a graphic image, the controller 56 generates a command associated with the graphic image. The graphic images 64–70 may be removed from the video image by drawing in air on the tube 46 and turning off the laser pointer 40.

The graphical image 68 may generate a command to create a "pointer" out of the cursor 72 so that any subsequent movement of the cursor 72 will not generate a corresponding movement of the robotic arm 20. The surgeon may use the pointer as an instructional aid for other personnel viewing the monitor 18.

The robotic arm 20 can be manipulated by initially placing the cursor 72 in the PAN graphic 70 and then moving the cursor 72 about the monitor 18. The interface controller 56 generates new pixel locations associated with the cursor movement which are then provided to the robot controller 60 to move the robotic arm so that the video image moves in conjunction with the movement of the cursor and the spatial location of the laser beam on the screen.

Figure 5:
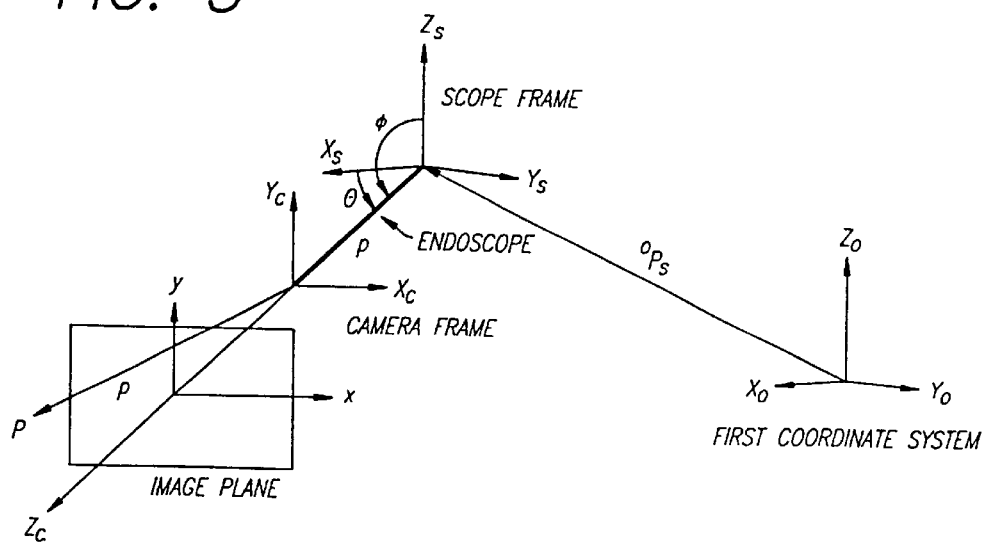
FIG. 5 is a schematic of an endoscope within various coordinate frames.

The process of moving the endoscope is performed by initially subtracting the new pixel position from an arbitrary reference pixel position to determine a $\Delta x$ and a $\Delta y$ pixel movement of the cursor 72 within the video image 62. The computed movement ($\Delta x$ and $\Delta y$) is multiplied by a weighted pseudoinverse of the following Jacobean matrix with reference to the coordinate system shown in FIG. 5.

$$\begin{bmatrix} \frac{-xy\sin\phi}{f} + y\cos\theta & \frac{-f\rho}{Z_c} - \left(f + \frac{x^2}{f}\right) & \frac{x}{Z_c} \\ -x\cos\theta - \sin\phi\left(f + \frac{y^2}{f}\right) - \frac{f\rho\sin\phi}{Z_c} & -\frac{xy}{f} & \frac{y}{Z_c} \end{bmatrix}$$

where;
the angles $\theta$, $\phi$ and $\rho$ are measured by robotic position sensors (not shown). The angles provide spherical coordinates of the endoscope within a scope frame coordinate system that has an origin at the pivot point of the instrument and the patient.
x, y=the new pixel coordinates of the reference point.
$Z_c$=is a constant.
f=the focal length of the endoscope lens.

The product ($V\theta$, $V\phi$ and $V\rho$) of the reference point movement ($\Delta x$ and $\Delta y$) and the Jacobean matrix is the computed movement of the endoscope by the robotic arm assembly in a spherical coordinate frame. The spherical coordinates ($V\theta$, $V\phi$ and $V\rho$) are converted into Cartesian coordinates (Vx, Vy and Vz) by a transformation. The movement of the endoscope within the scope frame is converted to the fixed first coordinate system by an additional transformation matrix or matrices.

Figure 6:
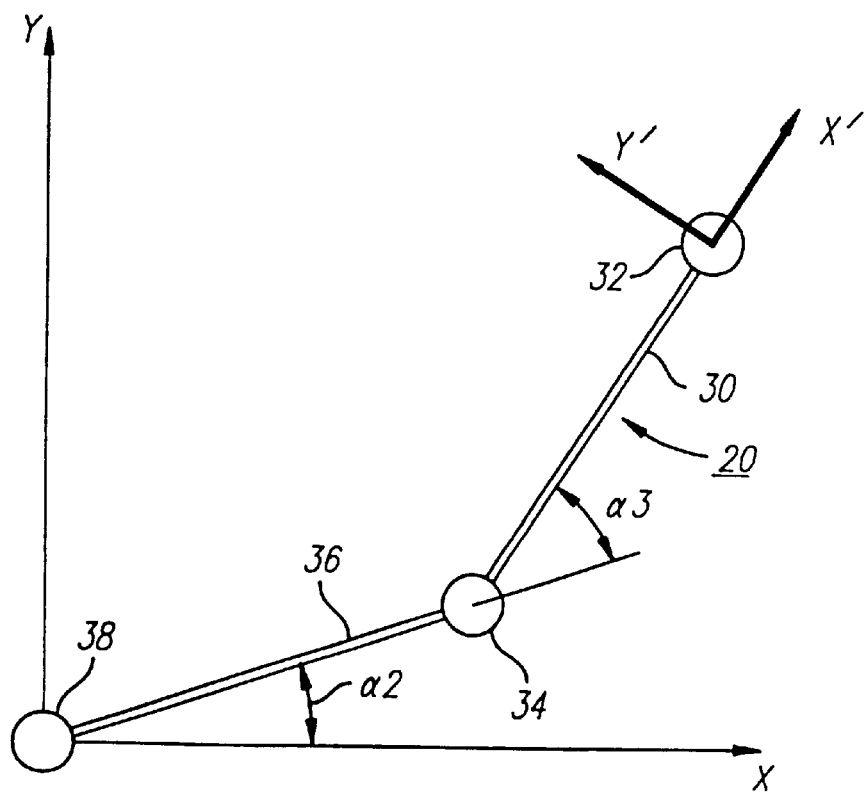
FIG. 6 is a schematic of a robotic arm.

Referring to FIG. 6, the controller 60 typically computes the movement of the robotic arm assembly 20 in accordance with the following equations.

$$a3 = \pi - \cos^{-1}\left(\frac{x^2 + y^2 - L1^2 + L2^2}{-2 \cdot L1 L2}\right)$$

$$\Delta = \cos^{-1}\left(\frac{x^2 + y^2 - L1^2 - L2^2}{2L1\sqrt{x^2 + y^2}}\right)$$

$$a0 = \tan^{-1} 2\left(\frac{y}{x}\right)$$

where;
a2=angle between the second linkage arm 36 and the x axis.
a3=angle between the first linkage arm 30 and the longitudinal axis of the second linkage arm 36.
L1=length of the second linkage arm.
L2=length of the first linkage arm.
x=x coordinate of the end effector in the first coordinate system.
y=y coordinate of the end effector in the first coordinate system.

To move the end effector to a new location of the x-y plane, the computer computes a change in the angles a2 and a3, and then provides output signals to move the actuators accordingly. The original angular position of the end effector is provided to the computer by the position sensors. The computer moves the linkage arms an angle that corresponds to the difference between the new location and the original location of the end effector. A differential angle $\Delta a2$ corresponds to the amount of angular displacement provided by the third actuator 38 and a differential angle $\Delta a3$ corresponds to the amount of angular displacement provided by the second actuator 34.

To improve the effectiveness of the system 10, the system is constructed so that the desired movement of the surgical instrument correlates to a direction relative to the image displayed by the monitor. Thus when the robotic arm moves the endoscope 12 up, the scope always appears to move in the up direction relative to the image displayed by the monitor. To accomplish this result, the computer converts the desired movement of the end of the endoscope in the third coordinate system to coordinates in the second coordinate system, and then converts the coordinates of the second coordinate system into the coordinates of the first coordinate system.

Referring to FIG. 2, the desired movement of the endoscope is converted from the third coordinate system to the second coordinate system by using the following transformation matrix;

$$\begin{pmatrix} \Delta x' \\ \Delta y' \\ \Delta z' \end{pmatrix} = \begin{pmatrix} \cos(a6) & 0 & -\sin(a6) \\ -\sin(a5)\sin(a6) & \cos(a5) & -\sin(a5)\cos(a6) \\ \cos(a5)\sin(a6) & \sin(a5) & \cos(a5)\cos(a6) \end{pmatrix} \begin{pmatrix} \Delta x'' \\ \Delta y'' \\ \Delta z'' \end{pmatrix}$$

where;
$\Delta x''$=the desired incremental movement of the scope along the x" axis of the third coordinate system.
$\Delta y''$=the desired incremental movement of the scope along the y" axis of the third coordinate system.
$\Delta z''$=the desired incremental movement of the scope along the z" axis of the third coordinate system.
a5=the angle between the z' axis and the scope in the y'-z' plane.
a6=the angle between the z' axis and the scope in the x'-z' plane.
$\Delta x'$=the computed incremental movement of the scope along the x' axis of the second coordinate system.
$\Delta y'$=the computed incremental movement of the scope along the y' axis of the second coordinate system.
$\Delta z'$=the computed incremental movement of the scope along the z' axis of the second coordinate system.

The angles a5 and a6 are provided by position sensors coupled on the end effector 32.

The desired movement of the endoscope is converted from the second coordinate system to the first coordinate system by using the following transformation matrix;

$$\begin{pmatrix} \Delta x \\ \Delta y \\ \Delta z \end{pmatrix} = \begin{pmatrix} \cos(\pi) & -\sin(\pi) & 0 \\ \sin(\pi) & \cos(\pi) & 0 \\ 0 & 0 & 1 \end{pmatrix} \begin{pmatrix} \Delta x' \\ \Delta y' \\ \Delta z' \end{pmatrix}$$

where;
$\Delta x'$=the computed incremental movement of the scope along the x' axis of the second coordinate system.

$\Delta y'$=the computed incremental movement of the scope along the y' axis of the second coordinate system.

$\Delta z'$=the computed incremental movement of the scope along the z' axis of the second coordinate system.

$\pi$=is the angle between the first linkage arm and the x axis of the first coordinate system.

$\Delta x$=the computed incremental movement of the scope along the x axis of the first coordinate system.

$\Delta y$=the computed incremental movement of the scope along the y axis of the first coordinate system.

$\Delta z$=the computed incremental movement of the scope along the z axis of the first coordinate system.

The incremental movements $\Delta x$ and $\Delta y$ are inserted into the algorithms described above for computing the angular movements ($\Delta a2$ and $\Delta a3$) of the robotic arm assembly to determine the amount of rotation that is to be provided by each actuator. The value $\Delta z$ is used to determine the amount of linear movement provided by the linear actuator 24.

The endoscope 12 is typically coupled to the camera 16 such that any spinning of the instrument about its own longitudinal axis will result in a corresponding rotation of the video image 62 on the monitor 18. Rotation of the instrument and video image may disorient the viewer. It is therefore desirable to maintain the orientation of the video image. In the preferred embodiment, the end effector has a worm gear which rotates the surgical instrument about the longitudinal axis of the instrument. To insure proper orientation of the endoscope, the worm gear rotates the instrument about its longitudinal axis an amount $\Delta\theta6$ to insure that the y" axis is oriented in the most vertical direction within the fixed coordinate system. $\Delta\theta6$ is computed from the following cross-products.

$$\Delta\theta6 = z_i" \times (yo" \times yi")$$

where;

$\Delta\theta6$=the angle that the instrument is to be rotated about the z" axis.

yo"=is the vector orientation of the y" axis when the instrument is in the first position.

yi"=is the vector orientation of the y" axis when the instrument is in the second position.

zi"=is the vector orientation of the z" axis when the instrument is in the second position.

The vectors of the yi" and zi" axis are computed with the following algorithms.

$$[zi"] = a5 \begin{bmatrix} \cos a6 & 0 & -\sin a6 \\ -\sin a5 \sin a6 & \cos a5 & -\sin a5 \cos a6 \\ \cos a5 \sin a6 & \sin a5 & \cos a5 \cos a6 \end{bmatrix} \begin{bmatrix} 0 \\ 0 \\ 1 \end{bmatrix}$$

$$xi" = z \times zi"$$

$$yi" = zi" \times xi"$$

where;

a6=is the angle between the instrument and the z axis in the y-z plane.

a5=is the angle between the instrument and the z axis in the x-z plane.

z=is the unit vector of the z axis in the first coordinate system.

The angles a5 and a6 are provided by the joint position sensors of the end effector. The vector yo" is computed using the angles a5 and a6 of the instrument in the original or first position. For the computation of yi", the angles a5 and a6 of the second position are used in the transformation matrix. After each arm movement yo" is set to yi" and a new yi" vector and corresponding $\Delta\theta6$ angle are computed and used to re-orient the endoscope. Using the above described algorithms, the worm gear continuously rotates the instrument about its longitudinal axis to insure that the pivotal movement of the endoscope does not cause a corresponding rotation of the viewing image.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although graphic images which provide commands to control a robotic arm are shown and described, it is to be understood that the graphics may generate commands that control other devices. The graphic overlay processor 58 may provide an entire menu that allows the surgeon to adjust the operating table or the lighting of the camera 16. Additionally, surgical instruments such as laser cutters or electrode coagulators may be controlled by the surgeon through the head activated graphical interface provided by the present invention. The present invention generally provides a remotely controlled graphically based interface that allows the surgeon to control various devices and conditions at a surgical site.

What is claimed is:

1. A medical system adapted to be coupled to an endoscope that is coupled to a monitor which displays a video image provided by the endoscope, the medical system comprising:

a robotic arm configured to be coupled to the endoscope; and an electrical circuit that is coupled to said robotic arm and being configured to overlay a graphic image onto the video image;

wherein the overlaid graphic image is adjustable to manipulate the video image.

2. The system of claim 1, wherein said electrical circuit overlays a dynamic graphic cursor onto the video image.

3. The system of claim 2, wherein the dynamic graphic cursor can be moved into the graphic image to select a function.

4. The system of claim 3, wherein the function is a movement of said robotic arm.

5. The system of claim 1 further comprising a controller configured to adjust the endoscope to manipulate the video image in response to adjustments to the overlaid graphic image.

6. The system of claim 1 wherein the graphic image comprises at least one of "in" for video zoom in, "out" for video zoom out, and "pan" for video pan movement.

7. A medical system adapted to be coupled to an endoscope that is coupled to a monitor which displays a video image provided by the endoscope, the medical system comprising:

movement means for moving the endoscope; and overlay means for overlaying a graphic image onto the video image;

wherein the overlaid graphic image is adjustable to manipulate the video image.

8. The system of claim 7, wherein said overlay means overlays a dynamic graphic cursor onto the video image.

9. The system of claim 8, wherein the dynamic graphic cursor can be moved into the graphic image to select a function.

10. The system of claim 9, wherein the function is a movement of said movement means.

11. The system of claim 7 further comprising control means for adjusting the endoscope to manipulate the video image in response to adjustments to the overlaid graphic image.

12. A method for operating a medical system, comprising:

moving an endoscope within a patient;

displaying a video image provided by the endoscope on a monitor coupled to the endoscope; and overlaying a graphic image onto the video image;

wherein the overlaid graphic image is adjustable to manipulate the video image.

13. The method of claim 12, further comprising selecting a function by moving a dynamic graphic cursor into the graphic image.

14. The method of claim 13, further comprising adjusting the endoscope in response to the selection of the function.

15. The method of claim 13 wherein the graphic image comprises at least one of an "in" function for video zoom in, an "out" function for video zoom out, and a "pan" function for video pan movement.

16. The method of claim 12 further comprising adjusting the endoscope to manipulate the video image in response to adjustments to the overlaid graphic image.

17. A medical system adapted to be coupled to an endoscope that is coupled to a monitor which displays a video image provided by the endoscope, the medical system comprising:

a robotic arm configured to be coupled to the endoscope;

an electrical circuit that is coupled to said robotic arm and being configured to overlay a dynamic graphic cursor and graphic image onto the video image; and a cursor input device coupled to said electrical circuit;

wherein the overlaid graphic image is adjustable by the dynamic graphic cursor to manipulate the video image.

18. The system of claim 17, wherein the dynamic graphic cursor can be moved into the graphic image to select a function.

19. The system of claim 18, wherein the function is a movement of said robotic arm.

20. The system of claim 17 further comprising a controller configured to adjust the endoscope to manipulate the video image in response to adjustments to the overlaid graphic image.

21. The system of claim 17 wherein the graphic image comprises at least one of "in" for video zoom in, "out" for video zoom out, and "pan" for video pan movement; and wherein the "in," "out," and "pan" are selectable by the dynamic graphic cursor.

22. A medical system adapted to be coupled to an endoscope that is coupled to a monitor which displays a video image provided by the endoscope, the medical system comprising:

movement means for moving the endoscope;

overlay means for overlaying a dynamic graphic cursor and a graphic image onto the video image; and input means for moving the dynamic graphic cursor;

wherein the overlaid graphic image is adjustable by the dynamic graphic cursor to manipulate the video image.

23. The system of claim 22, wherein the dynamic graphic cursor can be moved into the graphic image to select a function.

24. The system of claim 23, wherein the function is a movement of said movement means.

25. The system of claim 22 further comprising control means for adjusting the endoscope to manipulate the video image in response to adjustments to the overlaid graphic image.

* * * * *